US006537317B1

(12) United States Patent
Steinert et al.

(10) Patent No.: US 6,537,317 B1
(45) Date of Patent: Mar. 25, 2003

(54) BINOCULAR LENS SYSTEMS

(75) Inventors: Roger F. Steinert, North Andover, MA (US); Alan J. Lang, Long Beach, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/564,123

(22) Filed: May 3, 2000

(51) Int. Cl.[7] ................................................. A61F 2/16
(52) U.S. Cl. ..................................... 623/6.24; 623/6.28
(58) Field of Search .............................. 623/6.24, 6.27, 623/6.28; 351/161

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | De Carle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |

(List continued on next page.)

FOREIGN PATENT DOCUMENTS

| | | |
|---|---|---|
| AU | 3225789 | 10/1989 |
| DE | 2702117 | 7/1978 |
| DE | 3246306 | 6/1984 |
| EP | 939016 | 10/1963 |
| EP | 0246216 | 11/1987 |
| EP | 0342895 | 11/1989 |
| EP | 0351471 | 1/1990 |
| EP | 0566170 | 10/1993 |
| EP | 0691109 | 1/1996 |
| GB | 2129155 | 5/1984 |
| GB | 2148791 | 4/1985 |
| GB | 2192291 | 1/1988 |
| IL | 2058391 | 4/1981 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |

OTHER PUBLICATIONS

Jacobi, MD., et al, Arch Ophthalmol, vol. 117, pp. 17–23, Jan. 1999.

(List continued on next page.)

Primary Examiner—David H. Willse
Assistant Examiner—Javier G. Blanco
(74) Attorney, Agent, or Firm—Stout, Uxa, Buyan & Mullins, LLP; Frank J. Uxa; Peter Jon Gluck

(57) ABSTRACT

An binocular lens system for improving the vision of a patient including first and second ophthalmic lenses. Each of these lenses is adapted for implantation in an eye or to be disposed on or in the cornea. The first lens is biased for distance vision and the second ophthalmic lens is biased for near vision. The ophthalmic lenses may be intraocular lenses which are implanted in the eyes of a patient following removal of the natural lens.

31 Claims, 3 Drawing Sheets

U.S. PATENT DOCUMENTS

| | | |
|---|---|---|
| 4,199,231 A | 4/1980 | Evans |
| 4,210,391 A | 7/1980 | Cohen |
| 4,240,719 A | 12/1980 | Gullino et al. |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,638,211 A | 1/1987 | Neilsen et al. |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,704,016 A | 11/1987 | De Carle |
| 4,720,286 A | 1/1988 | Bailey et al. |
| 4,752,123 A | 6/1988 | Blaker |
| 4,759,762 A | 7/1988 | Grendhahl |
| 4,769,033 A | 9/1988 | Nordan |
| 4,813,955 A | 3/1989 | Achatz et al. |
| 4,830,481 A | 5/1989 | Futhey et al. |
| 4,881,804 A | 11/1989 | Cohen |
| 4,890,912 A | 1/1990 | Visser |
| 4,890,913 A | 1/1990 | De Carle |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,938,583 A | 7/1990 | Miller |
| 4,955,902 A | 9/1990 | Kelman |
| 4,976,534 A | 12/1990 | Miege et al. |
| 4,990,159 A | 2/1991 | Kraff |
| 5,002,382 A | 3/1991 | Seidner |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,476,514 A | 12/1995 | Cumming |
| 5,480,428 A | 1/1996 | Fedorov et al. |
| 5,496,366 A | 3/1996 | Cumming |
| 5,521,656 A | 5/1996 | Portney |
| 5,562,731 A | 10/1996 | Cumming |
| 5,574,518 A * | 11/1996 | Mercure ..................... 351/161 |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,776,191 A | 7/1998 | Mazzocco |
| 5,812,236 A * | 9/1998 | Seider et al. ............... 351/161 |
| 5,864,378 A * | 1/1999 | Portney ..................... 351/160 |
| 5,898,473 A * | 4/1999 | Seidner et al. ............. 351/161 |

OTHER PUBLICATIONS

IOL Technologie Brochure, MF4 The Autofocus Lens, 1995.
Menezo, et al. J. Cataract Refract Surg 24, Aug. 1998.
Fechner, et al. J. Cataract Refract Surg 24, Jan. 1998.
World Optics Inc. Ophthalmology Times, Mar. 15, 1995.
Lolab Corp, Ophthalmology Times, Mar. 15, 1995.
Universe IOL Center, Ocular Surgery News Int'l, No Date Given.
Hanita Lenses, Ocular Surgery News Int'l, No. Date Given.
Alcon Surgical, Alcon Laboratories, No Date Given.
Mediphacos LTDA. Ocular Surgery News, Int'l, No Date Given.
Storz Ophthalmics, Inc, Model L122UV ACL, No Date Given.
Opthalmed Inc, Omac–260, No Date Given.
Chauvin–Opsia, Azurite ACL (0459) No Date Given.
AMO Specs, Model AC–21B, 1992.
Chiron, Clemente Optifit Modell SPSP525 Brochure Translation, Dec. 1998.
Chrion Vision, Nuvita MA20, 1997.

* cited by examiner

BINOCULAR LENS SYSTEMS

BACKGROUND OF THE INVENTION

This invention relates to binocular lens systems which comprise ophthalmic lenses. The lenses may be adapted for implantation in an eye such as intraocular lenses(IOLS) or adapted to be disposed on or in the cornea such as contact lenses or corneal inlays.

When functioning normally, the natural lens of the eye is somewhat elastic and therefore enables good vision of objects at all distances. However, when the natural lens is removed as a result of disease or injury and replaced with an IOL, the natural ability of the eye to accommodate is lost completely. However, an ability to have adequate vision at different distances without using spectacles can be provided by the IOL which is implanted following removal of the natural lens. To this end, the IOL may be multifocal as shown and described, for example, in Portney U.S. Pat. No. 5,225,858, Roffman et al U.S. Pat. No. 5,448,312 or Menezes et al U.S. Pat. No. 5,682,223. Alterhatively, the IOL may be of the type which is accommodating in that it can be moved by the eye itself as shown and described in commonly assigned application Ser. No. 09/532,910 filed Mar. 22, 2000 or monofocal with a depth of focus feature as shown and described in Portney. U.S. Pat. No. 5,864,378.

Another approach to overcoming loss of accommodation is to use ophthalmic lenses, such as contact lenses or IOLS, with different optical characteristics for each eye. For example with a system known as monovision one lens has a distance vision correction power and the other lens has a near vision correction power. Another example is shown and described in Roffman et al U.S. Pat. No. 5,485,228. It is also known to implant a distant dominant multifocal IOL in one eye and a near dominant multifocal IOL in the other eye as disclosed in the January 1999 issue of Clinical Sciences by Jacobi et al entitled "Bilateral Implantation of Asymmetrical Diffractive Multifocal Intraocular Lenses," pages 17–23.

Ophthalmic multifocal lenses can also be provided with some depth of focus. This is shown and described, for example, in Portney U.S. Pat. No. 5,225,858 and Roffman et al U.S. Pat. No. 5,684,560.

Whether monovision or multifocal ophthalmic lenses are employed, nighttime images may not be the same for both eyes and/or possess halos as when the headlights of an oncoming vehicle are observed. This can significantly reduce the ability of the observer to identify and locate objects near the headlights. For example, halos tend to be created when the patient views a distant object through the near vision portion of a multifocal lens, and the greater the add power, the more perceptible is the halo.

For example, this is shown and described in commonly assigned application Ser. No. 09/302,977 filed on Apr. 30, 1999. This application discloses a reduced add power multifocal IOL which reduces the effects of halos. This reduced add power IOL is implanted in a phakic eye in which the natural lens has lost some degree of accommodation, i.e. in partially presbyopic eyes.

The disclosure of each of the patent applications and patents identified herein is incorporated in its entirety herein by reference.

SUMMARY OF THE INVENTION

New binocular ophthalmic lens systems have been discovered. The present lens systems provide a combined effect of enhancing distance, intermediate and near visual function. In particular, the lens system are very effective in enhancing intermediate vision. Other important advantages are obtained. In general, the present lens systems comprise two lenses. The ophthalmic lens systems of this invention may include first and second lenses for use with first and second eyes of a patient, respectively. Each of the first and second lenses has more than one vision correction power and is therefore multifocal. Although this invention is particularly adapted for IOLS, it is also applicable to lenses which can be disposed on or in the cornea such as contact lenses and corneal inlays.

One lens, the first lens, provides the best image quality for distance or distant objects. The other lens, the second lens, provides the best image quality for near objects. As such, the present lens systems operate.in part like a monofocal monovision pair. Each lens preferably contains a larger depth of focus than conventional monofocal lens designs. The depth of focus of the first lens preferably ranges from distance to intermediate distances. The depth of focus of the second lens preferably ranges from near to intermediate distances. The extended depth of focus is believed to reduce the disparity in functional vision eyes and to at least reduce the size and/or the occurrence of multifocal lens halos.

The first lens is biased for distance vision or distance biased. This may be accomplished, for example, by configuring the first lens so that the best visual acuity provided by the lens is for distant objects, for example, objects at infinity. The first lens provides better visual acuity for objects at infinity than the second lens. Preferably, the first lens substantially optimizes visual acuity from distance to intermediate distances. The first lens has a power including a maximum add power which is less than the add power for full near vision correction for the patient. Advantageously, the maximum add power of the first lens is no greater than about an add power for intermediate vision. The power of the first lens preferably varies from about the power for distance vision to the add power for intermediate vision. For example, the maximum add power of the first lens may be no more than about 1.5 diopters or about 1.75 diopters. All of the add powers set forth herein are in the spectacle plane. The first lens preferably has a power including a power required for distance vision correction for the patient.

The second lens is near biased. This may be accomplished, for example, by configuring the second lens so that the best visual acuity provided by the second lens is for objects at near distances. Alternatively, or in addition thereto, the second lens provides better visual acuity from intermediate to near distances, and in particular at near distances, than the first lens. Preferably, the second lens enhances visual acuity from intermediate to near distances. The second lens advantageously has a power including an add power for near vision. The minimum add power of the second lens preferably is no greater than about an add power for intermediate vision. In addition to the advantages noted above, the enhanced visual acuity of the second lens significantly enhances near vision and image quality.

The lenses can be made to have the relatively larger ranges of vision in various ways. For example, this can be accomplished by appropriately splitting the light between distance, intermediate and-near. Thus, the second lens may focus sufficient light to a near focus region so as to contribute to the second lens providing enhanced vision and better visual acuity from intermediate to near distance.

Alternatively or in addition thereto, the depth of focus of the zone or zones of the lens which provide intermediate vision correction may be appropriately increased to provide the second lens with enhanced vision characteristics from intermediate to near distances. This may be accomplished, for example, by controlling the aspheric surface design of the lenses. More specifically, the first and second lenses may each have a zone with an add power for intermediate vision correction with such zone having optical aberrations which increase the depth of focus of such zone. In one preferred embodiment, such zones extend radially outwardly and have progressively changing add powers as the zones extend radially outwardly.

The add power of the first lens is reduced over what it would be if the lens had the full or even nearly full add power, required for near vision correction. The reduced add power significantly reduces multifocal lens halos, such as those halos which occur in any eye because of the relatively large add power component, e.g., full or nearly full near vision add power, found in many multifocal lens designs.

In the interest of keeping the add power low while providing adequate vision quality, preferably the maximum add power of the first lens is no greater than about the power required for intermediate vision correction. By way of example, the maximum add power for the first lens may be from about 0.5 diopter to about 1.75 diopters and is preferably from about 1 diopter to about 1.5 diopters. The full or complete near vision correction can range from greater than about 1.75 diopters of add power, and is typically between about 2.0 diopters or about 2.5 diopters and about 3.0 or more diopters of add power.

The first and second lenses are adapted to provide some depth of focus. The first and second lenses preferably provide some depth of focus toward intermediate vision correction.

Each of the first and second lenses has an optical axis. Preferably the power of the first lens is different at a plurality of locations radially outwardly of the optical axis of the first lens, and the power of the second lens is different at a plurality of locations radially outwardly of the optical axis of the second lens.

Viewed from a different perspective, the power of each of the first and second lenses changes along a power curve, for example, in a radially outward direction from the associated optical axis. The power curve for the first lens is different from the power curve for the second lens. The power curve of the first lens may at least contribute to the first lens having good visual acuity from distance to intermediate distances and the power curve of the second lens may at least contribute to the second lens having good visual acuity from intermediate to near distances. The first lens may have a power which varies from about the power required for far vision correction to about a power required for intermediate vision correction. The second lens may have a power which varies from a power required for intermediate vision correction to a power required for near vision correction.

In one preferred embodiment, the first lens has first, second and third optical zones arranged radially with respect to the optical axis of the first lens with the second zone being intermediate or between the first and third zones and having a greater add power than either of the first and third zones. The second lens has first, second and third optical zones arranged radially with respect to the optical axis of the second lens with the second zone being intermediate or between the first and third zones and having a reduced add power than either of the first and third zones of the second lens.

Although the zones can be of various configurations, they are preferably substantially annular and substantially concentric. Preferably, there are at least two zones. Still more preferably, there are three or five of the zones with the innermost and outermost of the zones of the first lens having a power for far vision correction and the innermost and outermost of the zones of the second lens having a power for intermediate vision correction.

The power in a radial direction can change either gradually or abruptly. In one form of the invention, each of the second zones has a power which is substantially constant, and the area, for example, the annular area, of the second zone of the second lens is larger than the area of the second zone of the first lens. This also contributes to the second lens having better visual acuity from intermediate to near than the first lens.

IOLS constructed in accordance with this invention preferably are implanted following removal of the natural lenses, although they may be adapted for implantation in phakic eyes having some residual accommodation.

According to one aspect of the method of this invention, first and second ophthalmic lenses having different optical characteristics are placed on or in the eyes, respectively, of the patient. The first lens has better visual acuity for objects at infinity than the second lens. The second lens has better visual acuity for near distances than the first lens. The maximum add power of the first lens is less than the add power required for near vision correction. Preferably the ophthalmic lenses are IOLs and the step of placing includes implanting the first and second lenses in the eye, respectively, of the patient, for example, after removal of the patient's natural lenses.

According to another feature of the method of this invention, first and second IOLs having different optical characteristics are placed on or implanted in the eyes, respectively, of a patient. The first lens having a power which varies between about a far vision power and about an intermediate power, and having a maximum power which is less than the add power required for near vision for the patient. The second lens provides better visual acuity for objects at near distances than the first lens.

Although the first and second lenses of the present inventions may be contacts or corneal inlays, the features of this invention are particularly adapted for IOLS which can be implanted, respectively, in the eyes of the patient, preferably a patient whose natural lenses have been removed.

Any and all features described herein and combinations of such features are included within the scope of the present invention provided that the features of any such combination are not mutually inconsistent.

The invention, together with additional features and advantages thereof, may best be understood by reference to the following description taken in connection with the accompanying illustrative drawings.

DESCRIPTION OF THE PREFERRED EMBODIMENT

Figure 1:
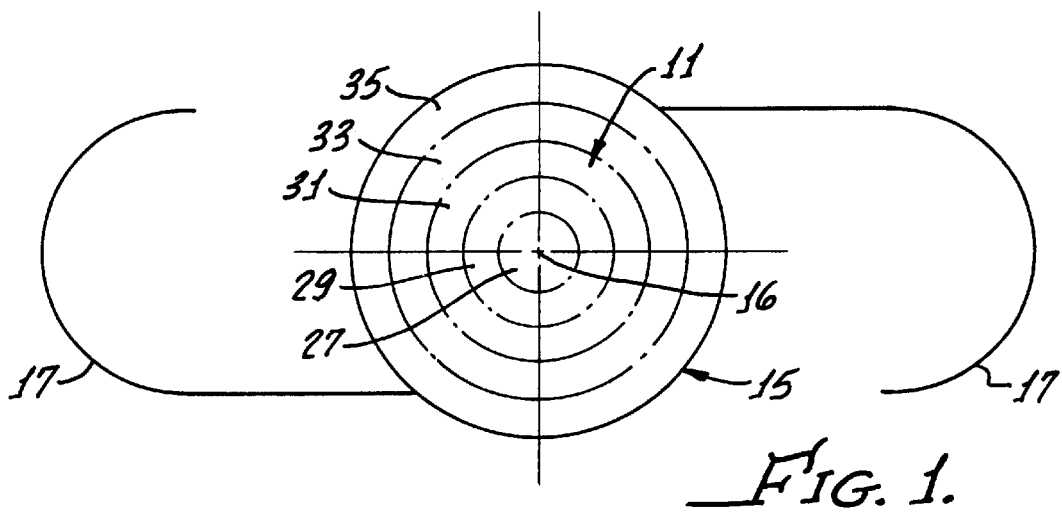
FIG. 1 is a somewhat schematic elevational view of one embodiment of an IOL constructed in accordance with this invention which is substantially optimized for distance-to-intermediate vision.
Figure 2:
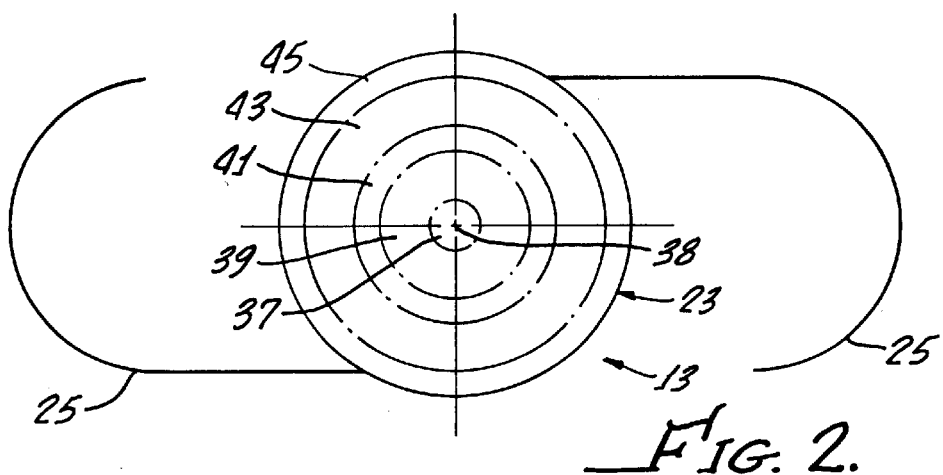
FIG. 2 is a view similar to FIG. 1 of one embodiment of an IOL constructed in accordance with this invention which is enhanced for near vision.

FIG. 1 shows an optimized distance-to-intermediate multifocal IOL 11 and FIG. 2 shows an enhanced near multifocal IOL 13 which together with the IOL 11 form a lens pair or ophthalmic lens system for improving the vision of a patient. The IOL 11 includes a multifocal lens body or optic 15 an optical axis 16 and having powers for a vision correction as described more fully herein below. The IOL 11 also includes generally radially extending fixation members 17 which, in this embodiment, are secured to the lens body 15.

A variety of configurations can be employed for the fixation members 17 in order to provide for effective fixation of the IOL 11 in the eye. If the IOL 11 is to be implanted following removal of the natural lens from the eye, then any of those configurations known in the art for that purpose may be employed. On the other hand, if the IOL 11 is to be implanted without removal of the natural lens from the eye, then the fixation members 17 should be of a configuration and construction which will allow the IOL 11 and the natural lens of the eye to usefully coexist in the eye. In that regard, any of the configurations shown by way of example in commonly assigned application Ser. No. 09/302,977, filed on Apr. 30, 1999 may be employed. The fixation members 17 may be made of materials of construction, such as polymeric materials, for example, acrylic; polypropylene, silicone, polymethylmethacrylate and the like, many of which are conventionally used in fixation members. In the embodiment shown each of the fixation members 17 has the form shown by way of example in FIGS. 1 and 3, and this adapts the IOL 11 for implantation in the capsular bag of the eye after removal of the natural lens.

The lens body 15 may be constructed of rigid biocompatible materials such as polymethylmethacrylate (PMMA), or flexible, deformable materials, such as silicone polymeric material, acrylic polymeric material, hydrogel polymeric material and the like, which enable the lens body. to be rolled or folded before insertion through a small incision into the eye. Although the lens body 15 shown in FIG. 1 is a refractive lens body, it may be diffractive if desired.

Figure 3:
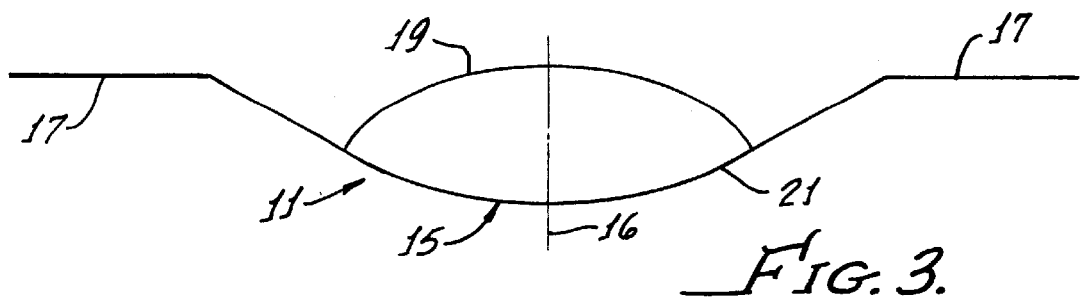
FIG. 3 is a side elevational view of the IOL of FIG. 1

As shown in FIG. 3, the lens body 15 has a convex anterior surface 19 and a convex posterior surface 21; however, these configurations are merely illustrative. Although the vision correction power may be placed on either of the surfaces 19 or 21, in this embodiment, the anterior surface 19 is appropriately shaped to provide the desired vision correction powers.

The IOL 13 similarly has a multifocal lens body 23 and fixation members 25 suitably joined to the lens body 23. The optical characteristics of the lens bodies 15 and 23 are different as described more specifically herein below. However, except for the optical characteristics of the lens bodies 15 and 23, the IOLs 11 and 13 may be identical.

With respect to optical characteristics, it can be seen from FIG. 1 that the IOL 11 has a central zone 27 and additional optical zones 29, 31, 33 and 35. In this embodiment, the central zone 27 is circular and the lens body 15 has a circular outer periphery. Also, in this embodiment, the additional optical zones 29, 31, 33 and 35 are annular and concentric with the central zone 27, and all of these zones are centered on the optical axis 16.

Figure 4:
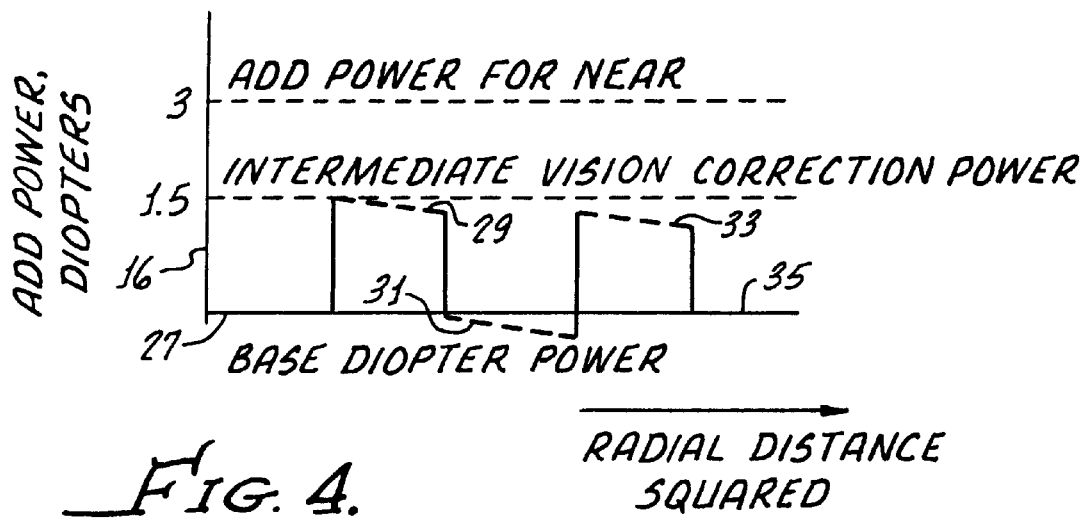
FIG. 4 is a plot of add power of the IOL of FIG. 1 versus radial distance squared from the optical axis of that IOL.
Figure 5:
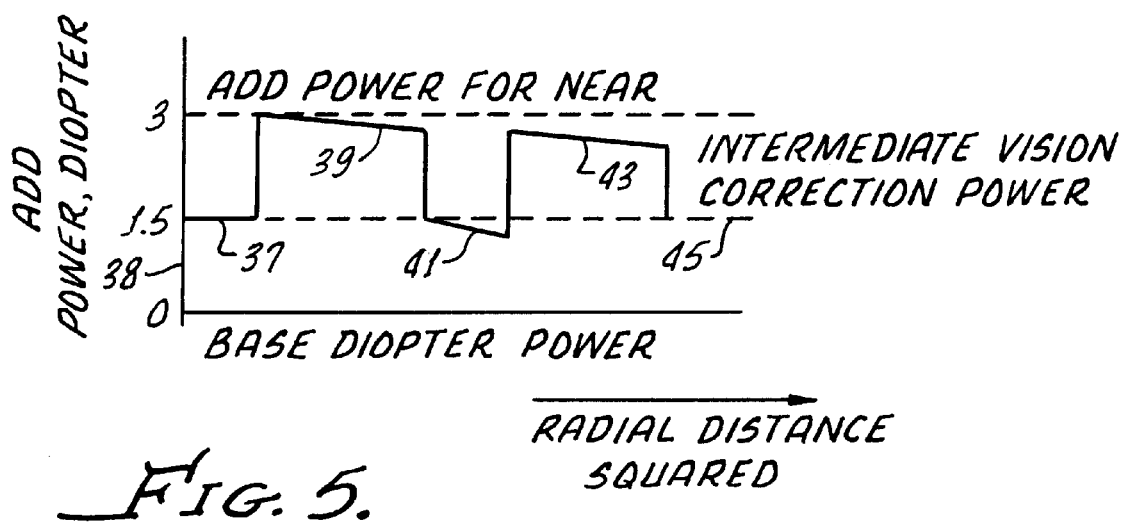
FIG. 5 is a plot similar to FIG. 4 for the IOL of FIG. 2.

With reference to FIG. 4, it can be seen that the central zone 27 and the outermost annular zone 35 have a base or baseline diopter power which is the power required by the patient for distance vision correction and is considered as a zero add power. It should also be noted that the diopter power variation shown in FIGS. 4 and 5 is applicable to any point on the surface of the lens bodies 15 and 23, respectively, at a fixed radial distance from the associated optical axes. In other words, the power at any given radial distance from the optical axis 16 is the same, and the power at any given radial distance from the optical axis 38 is the same.

The annular zone 31 has about the power required for distance vision correction. Although the annular zone 31 could have precisely the power required for distance vision correction, i.e. zero add power, in this embodiment, the power of the annular zone 31 decreases progressively and slightly from the outer edge of the zone 29 to about the inner edge of the zone 33 to provide spherical aberration correction. Thus, although the optical power of the zone 31 does diminish in a radial outward direction in this fashion, it nevertheless is considered to be about the power needed for far or distance vision correction for the patient. For example, the vision correction power of the zone 31 may decrease from a zero add power to about 0.25 diopter below the base diopter power.

The zones 29 and 33 have greater vision correction power than the zones 27, 31 and 35 and are preferably at or about the power required for intermediate vision correction. In terms of a single power, the power for intermediate vision correction would be halfway between the base diopter power and the add power for near vision correction. By way of example, if the base diopter power is considered to be zero add and the add power for near vision correction is considered to be 3 diopters, then the power for intermediate vision correction would be 1.5 diopters of add power. More broadly, however, the intermediate vision correction power may be taken to embrace a zone of from about 0.5 diopter to about 1.75 diopters and preferably that zone may be from about 1 diopter to about 1.5 diopters. When-thus considered, the, power of the zones 29 and 33 would all be add powers for intermediate vision correction.

The vision correction power in the zone 29 reduces progressively and slightly in a radial outward direction from an add power for intermediate vision correction such as 1.5 diopters as shown in FIG. 4 to a slightly less add power for intermediate vision correction so as to provide for spherical aberration correction. Again, to correct for spherical aberration, the maximum power of the zone 33 is less than the, minimum power of the zone 29 and reduces progressively and slightly in a radial outward direction as shown in FIG. 4. By way of example, the power of the zone 29 may decrease linearly from about 1.5 diopters to about 1.25 diopters and the vision correction power of the zone 33 may reduce linearly in a radial outward direction from about 1.0 diopter to about 0.75 diopter. Thus, all of the powers of the zones 29 and 33 may be considered as add powers for intermediate vision correction. Thus, it can be readily seen from FIG. 4 that the maximum power of any region of the first lens is no greater than about the power for intermediate vision correction.

The annular areas of the distance correction zones 27, 31 and 35 are intended to be larger than the annular areas of the intermediate power zones 29 and 33. Moreover, there are three of the distance power zones 27 and 35 and only two of the intermediate vision correction zones 29 and 33, although other numbers of these zones may be employed, if desired. Thus, a larger surface of the lens body 15 is dedicated to focusing or directing light to a far focus region than any other focus region. Accordingly, the IOL 11 provides very good visual acuity from distance to intermediate, and provides better visual acuity for objects at infinity than the IOL 13. The IOL 11 is optimized for distance to intermediate vision.

The lens body 23 of the IOL 13 has a circular outer periphery, an optical axis 38, a circular central zone 37 and optical zones 39, 41, 43 and 45 which are preferably annular and concentric with the central zone 37. All of these zones 37, 39, 41, 43 and 45 are centered on the optical axis 38. The nature of the optical zones 37, 39, 41, 43 and 45 makes the lens body 23 optically different from the lens body 15, but except for this the IOLs 11 and 13 may be identical, if desired.

It can be seen from FIG. 5 that the central zone 37 and the outer annular zone 45 have an add power for intermediate vision, that is about a power required for intermediate vision correction for the patient. The intermediate annular zone 41 has about this intermediate add power. More specifically, zones 37, 41 and 45 each has an add power which is an intermediate diopter power. Such zones 37, 41 and 45 facilitate the IOL 13 providing good vision between intermediate and near.

The annular zone 41 has the power required for intermediate vision correction. In this embodiment, the power of the annular zone 41 decreases progressively and slightly from the outer edge of the zone 39 to about the inner edge of the zone 43 to provide spherical aberration correction. Thus, although the optical power of the zone 41 does diminish in a radial outward direction in this fashion, it nevertheless is considered to be the power needed for intermediate vision correction for the patient. For example, the vision correction power of the zone 41 may decrease from a 1.5 diopters add power to about 1.25 diopters add power.

The zones 39 and 43 have a vision correction power which is about the add power for near vision correction.

The vision correction power in the zone 39 reduces progressively and slightly in a radial outward direction from an add power for near vision correction such as 3 diopters as shown in FIG. 5 to a slightly less add power for near vision correction so as to provide for spherical aberration correction. Again, to correct for spherical aberration, the maximum power of the zone 43 is about the minimum power of the zone 39 and reduces progressively and slightly in a radial outward direction as shown in FIG. 5. By way of example, the power of the zone 39 may decrease linearly from about 3 diopters to about 2.75 diopters and the vision correction power of the zone 43 may reduce linearly in a radial outward direction from about 2.75 diopters to about 2.55 diopters. Thus, all of the powers of the zones 39 and 43 may be considered as add powers for near vision correction.

In this embodiment, the IOL 13 has enhanced intermediate to near vision, and particularly enhanced near vision.

In addition a larger portion of the area of the lens body 23 is used to direct light to near focus region so as to contribute to the lens body 23 having better visual acuity from intermediate to near, and in particular near, than the IOL 11. Thus, the combined areas, that is the combined annular areas, of the zones 39 and 43 are greater than the combined areas of the zones 37, 41 and 45, and this is shown in FIG. 5. Consequently, more of the incident light is directed to near focus region than to an intermediate focus region, and this also contributes to the IOL 13 providing better visual acuity from intermediate to near than the IOL 11 and to providing enhanced intermediate-to-near, and in particular near, image quality. As compared with the IOL 11, it can also be seen from FIGS. 4 and 5 that the area of each of the zones 39 and 43 of the IOL 13 is larger than the area of either of the zones 29 and 33 of the IOL 11. This also contributes to the IOL 13 having better visual acuity from intermediate to near than the IOL 11. IOL 13 is near biased, whereas IOL 11 is distance biased.

From FIGS. 4 and 5, it is apparent that the maximum powers of any region of the IOL 11 are less than the add power required for full near vision correction, the latter being an add power which is at least greater than 1.75 diopters and may be 2.5 or 3.0 diopters. Also, the maximum powers of any region of the IOL 11 are no greater than about the intermediate vision correction power. Conversely, the minimum powers of any region for the IOL 13 is no less than about the intermediate vision correction power. The plots of FIGS. 4 and 5 represent power curves showing how the vision correction power of each of the IOLs 11 and 13 changes in a radially outward direction from the optical axes 16 and 38, respectively, and it is apparent that the power curves of FIGS. 4 and 5 are different. Moreover, the differences in these power curves contribute to the range of vision and visual acuity characteristics of IOLs 11 and 13.

FIGS. 1–3 illustrate one way that this invention may be embodied in IOLs. However, the invention may also be embodied in ophthalmic lenses which are adapted to be disposed on or in the cornea such as contact lenses and corneal inlays. The lens bodies 15 and 23 of FIGS. 1 and 2 may also be considered as schematically representing contact lenses or corneal inlays. Of course, these latter two forms of ophthalmic lenses do not have the fixation members 17 or 25.

This invention also provides a method of correcting the vision of a patient which comprises placing first and second multifocal ophthalmic lenses on or in the eyes of a patient with the first lens being distance biased and providing better visual acuity for objects at infinity than the second lens. The second lens is near biased and provides better visual acuity from intermediate to near, and in particular near, distances than the first lens. The maximum power of the second lens is about the add power required for near vision correction for the patient. With specific reference to the embodiments shown in FIGS. 1–3, the method includes implanting the IOLs 11 and 13 in the eyes, respectively, of the patient. This implantation preferably follows the removal of the natural lens from the eye.

The IOL 11 is implanted in capsular bag with the fixation members 17 in contact with the capsular bag. The natural lens has been removed from the eye. The IOL 13, which has optical characteristics different from the IOL 11, is similarly implanted in the other eye, with the natural lens removed, of the patient.

Figure 6A:
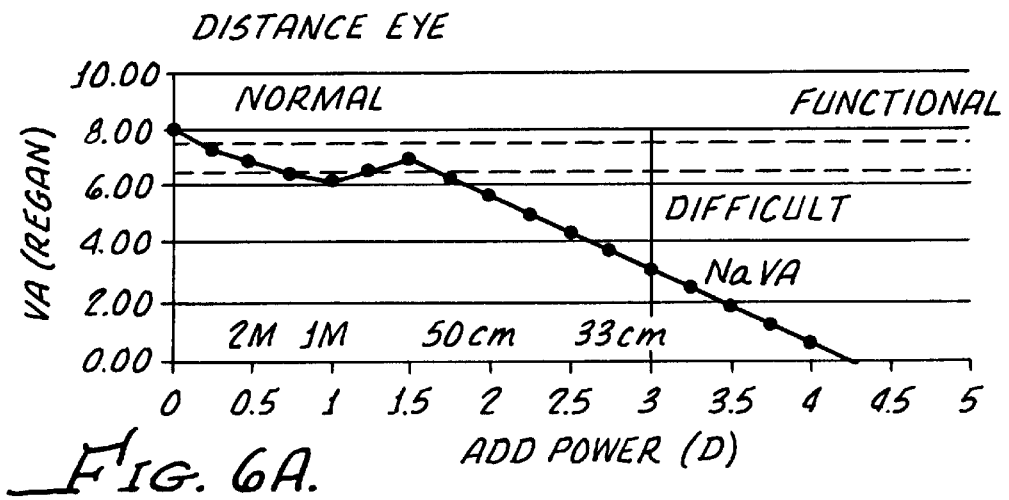
FIG. 6A is a plot of visual acuity versus add power for the IOL of FIG. 1 when implanted in an eye of a patient after removal for the natural lens.
Figure 6B:
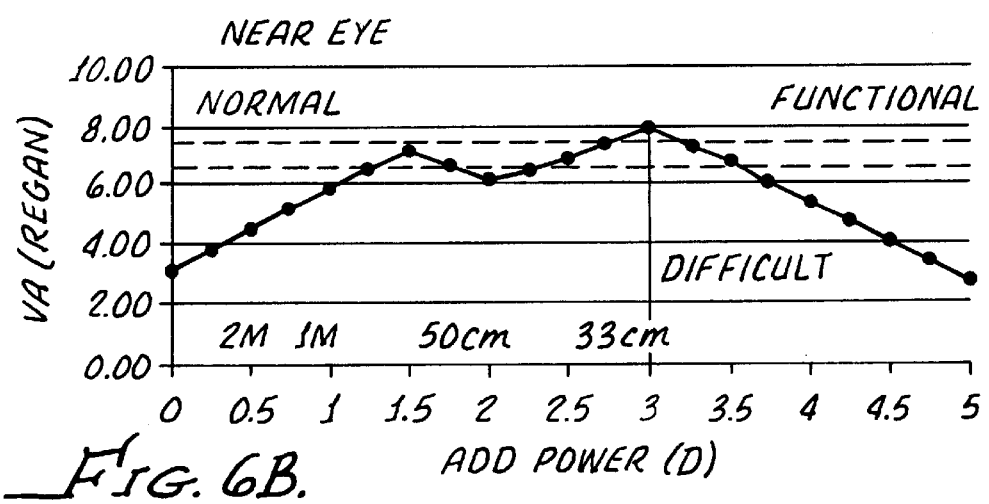
FIG. 6B is a plot similar to FIG. 6A for the IOL of FIG. 2 when implanted in an eye of a patient after removal of the natural lens.
Figure 6C:
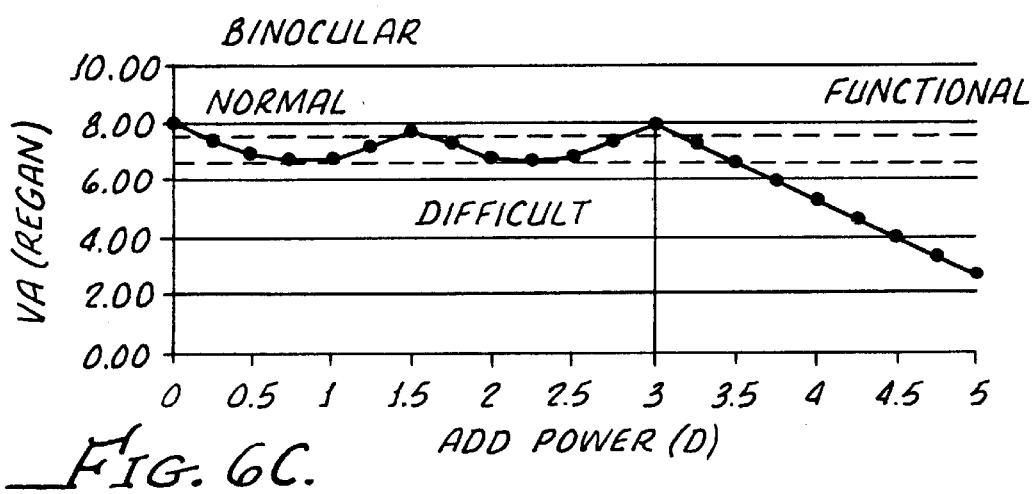
FIG. 6C is a plot similar to FIG. 6A for binocular vision when the IOLs of FIGS. 1 and 2 are implanted in the eyes, respectively, of a patient after removal of the natural lenses.

FIGS. 6A–C are of use in gaining a further understanding of how the IOLs 11 and 13 work. These figures are through-focus-acuity charts for a pseudophakic patient (with no natural accommodation) with these IOLs implanted. Each of these figures shows visual acuity (VA) along the ordinate and add power in diopters along the abscissa. In addition, the reciprocal of the diopter add power in meters is also shown along the abscissa. The add power is the add power required by a patient with no accommodation at the corresponding distance indicated on the abscissa. The units for visual acuity or VA are Regan. A visual acuity of about 8 corresponds to 20/20 and is considered normal vision. Functional vision is considered to be about 20/30 up to nearly 20/20, and is shown by the cross hatched or dashed line enclosed band in FIGS. 6A–C. Although functional vision is clinically not normal, it may seem normal to the patient. Below about 20/30 vision becomes progressively more difficult and somewhere about 3 Regan or slightly worse than 20/60 there, is essentially no usable visual acuity. The visual acuity plots of FIGS. 6A–C are theoretical.

The IOL 11 (FIG. 6A) has better visual acuity at infinity than does the IOL 13 (FIG. 6B) as shown by the higher visual acuity at the ordinate. The IOL 11 optimizes visual acuity from distance to intermediate distances as shown by the normal and functional visual acuity (FIG. 6A) from infinity to about 1.75 diopters of add power or about 57 centimeters. By comparing FIGS. 6A and 6B, it can be seen that the IOL 13 provides better visual acuity from intermediate to near, and in particular, near distances than does IOL 11 and that visual acuity in this range is enhanced. Also, by comparing FIGS. 6A and 6B, it can be seen that the IOL 13 provides better visual acuity for objects at near distances than the IOL 11. FIG. 6B shows that the best visual acuity provided by the IOL 13 is for objects at near distances such as about 30 cm which corresponds to 3.0 diopters of add power.

The binocular visual acuity remains functional or better for distance and intermediate objects. In addition, near reading between 40 centimeters and 33 centimeters is functional or better. Thus, the pseudophakic, patient should perform all tasks well.

While this invention has been described with respect to various specific examples and embodiments, it is to be understood that the invention is not limited thereto and that it can be variously practiced within the scope of the following claims.

What is claimed is:

1. An ophthalmic lens system for improving the vision of a patient comprising:
    a first intraocular lens for use with one eye of the patient said first lens having an optical axis and first, second and third optical zones arranged radially with respect to the optical axis, the second zone being intermediate the first and third zones.and having a greater add power than either of the first and third zones, the maximum add power of the first intraocular lens being no greater than about 1.75 diopters;
    a second intraocular lens for use with the other eye of the patient said second, lens having an optical axis and first, second and third optical zones arranged radially with respect to the optical axis of the second lens, the second zone of the second lens being intermediate the first and third zones of the second lens and having a greater add power than either of the first and third zones of the second lens, the first and third zones having an add power about an add power required for intermediate vision; and
    the first lens providing better visual acuity for objects at infinity than the second lens and the second lens providing better visual acuity from intermediate to near distance than the first lens.

2. An ophthalmic lens system as defined in claim 1 wherein the optical zones of the first lens are substantially annular and substantially concentric.

3. An ophthalmic lens system as defined in claim 1 wherein the first, second and third optical zones of the second lens are substantially annular and substantially concentric.

4. An ophthalmic lens system as defined in claim 1 wherein one of said zones of the second lens has an add power required for intermediate vision.

5. An ophthalmic lens system as defined in claim 1 wherein the second lens directs sufficient light to a near focus region so as to contribute to the second lens having said better visual acuity from intermediate to near distances.

6. An ophthalmic lens system as defined in claim 1 wherein the area of said second zone of the second lens is larger than the area of said second zone of the first lens.

7. An ophthalmic lens system as defined in claim 1 wherein said second zone of the second lens extends radially outwardly and has progressively decreasing vision correction powers as said zone extends radially outwardly.

8. An ophthalmic lens system for improving the vision of a patient comprising:
    first multifocal ophthalmic lens for use with one eye of a patient, said first lens having a power including a maximum add power which is less than the add power required for full near vision correction for the patient;
    a second multifocal ophthalmic lens for use with the other eye of the patient, said second lens having a central optical axis and an innermost zone including and surrounding the optical axis and having a maximum vision correction power which is less than the add power required for full near vision correction for the patient, the minimum add power of said second lens is no less than about an add power for intermediate vision;
    said second lens providing better visual acuity for objects at near distances than said first lens; and
    each, of said first and second lenses being adapted for implantation in an eye or to be disposed on or in a cornea of an eye.

9. An ophthalmic lens system as defined in claim 1 wherein the maximum add power of the first lens is no greater than about an add power for intermediate vision.

10. An ophthalmic lens system as defined in claim wherein the first lens provides better visual acuity for objects at infinity than the second lens.

11. An ophthalmic lens system as defined in claim 8 wherein the best visual acuity provided by the second lens is for an object at a near distance.

12. An ophthalmic lens system as defined in claim 8 wherein the second lens has a power including an add power for intermediate vision.

13. An ophthalmic lens system as defined in claim 8 wherein the second lens has a plurality of annular optical zones, a first of said zones having an add power for intermediate vision and a second of said zones having a power which is different from said add power for intermediate vision.

14. An ophthalmic lens system as defined in claim 8 wherein the power of the first lens varies from about said power for distance vision to about an add power for intermediate vision.

15. An ophthalmic lens system as, defined in claim 8 wherein the second lens has a power which varies from about an add power for near vision to about an add power for intermediate vision.

16. An ophthalmic lens system as defined in claim 8 wherein the maximum add power of the first lens is no more than about 1.75 diopters.

17. An ophthalmic lens system as defined in claim 8 wherein the first and second lenses are intraocular lenses.

18. An ophthalmic lens system as defined in claim 8 wherein the first and second lenses are contact lenses.

19. An ophthalmic lens system as defined in claim 8 wherein the first and second lenses are corneal inlays.

20. An ophthalmic lens system for improving the vision of a patient comprising:

a first multifocal ophthalmic lens for use with one eye of a patient, said first lens having a power including a power for distance vision and a maximum add power which is less than the add power required for full near vision correction for the patient;

a second multifocal ophthalmic lens for use with the other eye of the patient, said second lens having a central optical axis and an innermost zone including and surrounding the central optical axis and having an add power for intermediate vision;

said first lens providing better visual acuity for objects at infinity than the second lens; and each of said first and second lenses being adapted for implantation in an eye or to be disposed on or in a cornea of an eye.

21. An ophthalmic lens system as defined in claim 20 wherein the maximum add power of any region of the first lens is greater than about an-add power for intermediate vision.

22. An ophthalmic lens system as defined in claim 20 wherein the minimum add power of any region of the second lens. is no less than about an add power for intermediate vision.

23. An ophthalmic lens system for improving the vision of a patient comprising:

a first multifocal intraocular lens for use with one eye of a patient, said first intraocular lens having three power zones, each of the power zones having a different power than the adjacent power zone or zones, said first intraocular lens having a power including a power required for distance vision for the patient and a maximum add power which is less than the add power required for full near vision correction for the patient;

a second multifocal intraocular lens for use with the other eye of the patient and having an innermost zone having a maximum add power which is less than the add power required for full near vision correction for the patient, the second intraocular lens having a minimum add power no less than about an add power for intermediate vision; and the first intraocular lens having better visual acuity for objects at infinity than the second intraocular lens and the second intraocular lens having better visual acuity for objects at near distances than the first intraocular lens.

24. An ophthalmic lens system as defined in claim 23 wherein the maximum add power of the first intraocular lens is no greater than about the power required for intermediate vision correction.

25. An ophthalmic lens system comprising:

first and second intraocular lenses for use with first and second eyes of a patient, respectively, each of said first and second lenses having an optical axis;

the power of each of said first and second intraocular lenses changing along a power curve in a radially outward direction from the associated optical axis and the power curve for said first intraocular lens being different from the power curve for the second intraocular lens;

the maximum add power of said first intraocular lens being less than the add power required for full near vision correction; and said second intraocular lens having an innermost zone including and surrounding the optical axis, the innermost zone has a maximum add power less than the add power required for full near vision correction, said second intraocular lens having a minimum add power no less than about an add power for intermediate vision.

26. The ophthalmic lens system as defined in claim 25 wherein the power of the first intraocular lens varies from about a power required for distance vision correction to said maximum add power which is about a power required for intermediate vision correction.

27. An ophthalmic lens system as defined in claim 25 wherein the second intraocular lens has an optical zone with an add power for intermediate vision.

28. A method of correcting the vision of a patient comprising:

placing first and second multifocal ophthalmic lenses on or in the eyes of the patient, respectively, with the first lens having better visual acuity for objects at infinity than the second lens, the second lens having a central optical axis and an innermost zone including and surrounding the optical axis and having a maximum vision correction power which is less than the add power required for full near vision correction for the patient, the second lens further having better visual acuity for near distances than the first lens, the maximum add power of the first lens being less than the add power required for near vision correction and the second lens having a minimum add power no less than about an add power for intermediate vision.

29. The method of claim 28 wherein the first and second lenses are intraocular lenses and the step of placing includes implanting the first and second lenses in the eyes, respectively, of the patient.

30. The method of claim 28 wherein the step of placing includes placing the first and second lenses on or in the corneas, respectively, of the patient.

31. A method of correcting the vision of a patient comprising:

implanting first and second intraocular lenses having different optical characteristics in the eyes, respectively, with said first lens having three power zones with powers which vary between about a far vision power and about an intermediate vision power and a maximum power which is less than the add power required for near vision for the patient and with the second lens having an innermost zone having a maximum add power which is less than the add power required for full near vision correction for the patient, the second intraocular lens having a minimum add power no less than about an add power for intermediate vision and providing better visual acuity for objects at near distances than the first lens.

* * * * *